US 7,731,745 B2

(12) United States Patent
Yang et al.

(10) Patent No.: US 7,731,745 B2
(45) Date of Patent: Jun. 8, 2010

(54) FLEXIBLE, STRETCHABLE COILED-SHEET STENT

(75) Inventors: Yi Yang, San Francisco, CA (US);
Farhad Khosravi, San Mateo, CA (US);
Himanshu N. Patel, San Jose, CA (US)

(73) Assignee: Boston Scientific Cupertino Corp., Cupertino, CA (US)

( * ) Notice: Subject to any disclaimer, the term of this patent is extended or adjusted under 35 U.S.C. 154(b) by 510 days.

(21) Appl. No.: 10/960,328

(22) Filed: Oct. 6, 2004

(65) Prior Publication Data

US 2005/0049687 A1    Mar. 3, 2005

Related U.S. Application Data

(63) Continuation of application No. 09/347,845, filed on Sep. 30, 1999, now abandoned.

(51) Int. Cl.
*A61F 2/06* (2006.01)
*A61M 29/00* (2006.01)

(52) U.S. Cl. ...................... 623/1.15; 606/108
(58) Field of Classification Search ................ 623/1.15, 623/1.11, 1.44; 606/108, 191, 194, 195
See application file for complete search history.

(56) References Cited

U.S. PATENT DOCUMENTS

| 4,762,128 A | 8/1988 | Rosenbluth |
| 4,830,003 A | 5/1989 | Wolff et al. |

(Continued)

FOREIGN PATENT DOCUMENTS

| DE | 198 34 956 A1 | 5/1999 |
| EP | 0566807 | 10/1993 |
| EP | 0382014 | 12/1994 |
| WO | 95/31945 | 11/1995 |
| WO | WO 98/35634 | 8/1998 |
| WO | 98/58600 | 12/1998 |

OTHER PUBLICATIONS

EPO Publication No. EP 0 956 832 A1, Jacob Ricter, et al., "Bifurcated Stent with Improved Side Branch Aperture and Method of Making Same", Apr. 28, 1999.

(Continued)

*Primary Examiner*—Vy Q Bui
(74) *Attorney, Agent, or Firm*—Vidas, Arrett & Steinkraus P.A.

(57) ABSTRACT

A coiled-sheet stent includes a tubular body having a longitudinal axis and a circumference, and a plurality of cylindrical bands formed in the tubular body, each band having a zig-zag pattern including a series of sequential diagonal elements connected to one another and extending about the circumference. A plurality of longitudinal connectors extend between and connect adjacent bands. The diagonal elements have an arcuate shape, all diagonal elements in each band being oriented in either a clockwise or counter-clockwise direction about the circumference. The tubular body is expandable between contracted and enlarged conditions, and the zig-zag pattern is expandable between unstretched and unstretched conditions, the zig-zag pattern being biased towards the stretched condition above a transition temperature, thereby at least partially defining the enlarged condition. A multi-cellular stent structure is also provided that includes a plurality of bat shaped cells formed in a tubular body, each cell defining a head region, a tail region and opposing curved wing regions, and a plurality of connectors extending between and connecting adjacent cells. The head and tail regions of adjacent cells are directly connected to one another, and connectors extend between adjacent wing regions of adjacent cells.

17 Claims, 2 Drawing Sheets

U.S. PATENT DOCUMENTS

| | | | |
|---|---|---|---|
| 4,950,227 A | 8/1990 | Savin et al. | |
| 4,994,071 A | 2/1991 | MacGregor | |
| 5,019,085 A | 5/1991 | Hillstead | |
| 5,035,706 A | 7/1991 | Giantureo et al. | |
| 5,102,417 A | 4/1992 | Palmaz | |
| 5,135,536 A | 8/1992 | Hillstead | |
| 5,158,548 A | 10/1992 | Lau et al. | |
| 5,282,824 A | 2/1994 | Gianturco | |
| 5,330,500 A | 7/1994 | Song | |
| 5,354,308 A | 10/1994 | Simon et al. | |
| 5,395,390 A | 3/1995 | Simon et al. | |
| 5,405,377 A | 4/1995 | Cragg | |
| 5,443,498 A | 8/1995 | Fontaine | |
| 5,443,500 A | 8/1995 | Sigwart | |
| 5,449,373 A | 9/1995 | Pinchasik et al. | |
| 5,540,712 A | 7/1996 | Kleshinski et al. | |
| 5,643,312 A | 7/1997 | Fischell et al. | |
| 5,649,952 A | 7/1997 | Lam | |
| 5,665,115 A | 9/1997 | Cragg | |
| 5,733,303 A * | 3/1998 | Israel et al. | 623/1.15 |
| 5,746,765 A | 5/1998 | Kleshinski et al. | |
| 5,755,734 A | 5/1998 | Richter et al. | |
| 5,766,237 A | 6/1998 | Cragg | |
| 5,776,183 A | 7/1998 | Kanesaka et al. | |
| 5,788,979 A | 8/1998 | Alt et al. | |
| 5,807,404 A * | 9/1998 | Richter | 623/1.16 |
| 5,824,045 A | 10/1998 | Alt | |
| 5,824,054 A * | 10/1998 | Khosravi et al. | 623/1.44 |
| 5,836,964 A | 11/1998 | Richter et al. | |
| 5,843,117 A | 12/1998 | Alt et al. | |
| 5,843,120 A | 12/1998 | Israel et al. | |
| 5,843,175 A | 12/1998 | Frantzen | |
| 5,843,176 A | 12/1998 | Weier | |
| 5,855,600 A | 1/1999 | Alt | |
| 5,860,999 A | 1/1999 | Schnepp-Pesch et al. | |
| 5,868,782 A | 2/1999 | Frantzen | |
| 5,871,437 A | 2/1999 | Alt | |
| 5,871,538 A | 2/1999 | Dereume | |
| 5,895,406 A * | 4/1999 | Gray et al. | 623/1.15 |
| 5,954,743 A | 9/1999 | Jang | |
| 5,972,018 A | 10/1999 | Israel et al. | |
| 6,017,365 A | 1/2000 | Von Oepen | |
| 6,042,597 A | 3/2000 | Kveen et al. | |
| 6,099,561 A * | 8/2000 | Alt | 623/1.44 |
| 6,193,747 B1 * | 2/2001 | von Oepen | 623/1.15 |
| 6,224,626 B1 * | 5/2001 | Steinke | 623/1.16 |

OTHER PUBLICATIONS

PCT Publication No. WO 00/28921, Farhad Khosravi, et al., "Coiled-Sheet Stent-Graft with Exo-Skeleton", Nov. 8, 1999.

Giovanni Rolando, et al., EPO Publication No. EP 0 806 190 A1, "An Angioplasty Stent", Nov. 12, 1997.

Timothy J. Ley, et al., PCT Publication No. WO 99/44543, "Improved Stent Cell Configurations", Sep. 10, 1999.

Randolf Von Oepen, PCT Publication No. WO 98/35634, "Stent", Aug. 20, 1998.

* cited by examiner

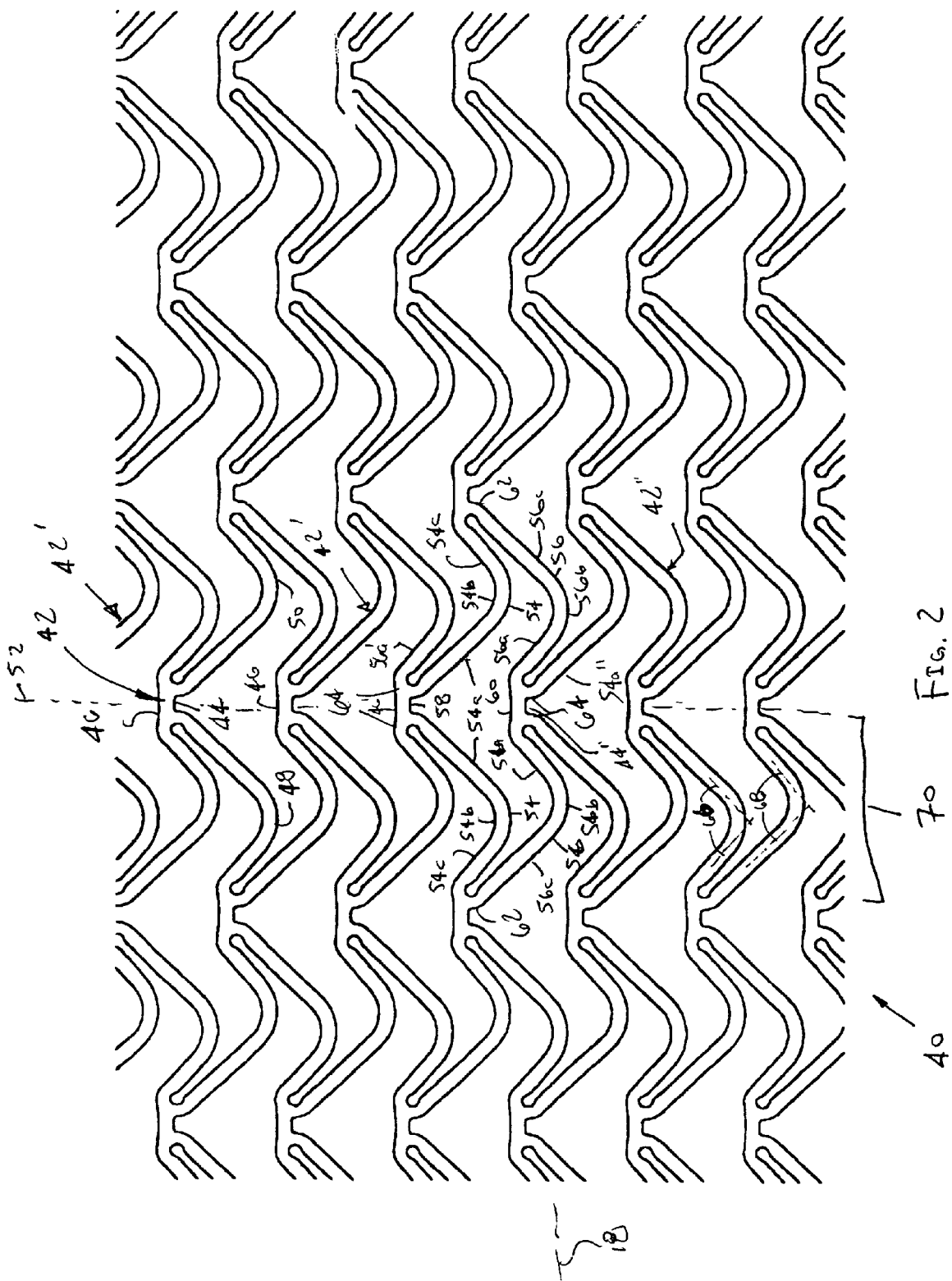

FLEXIBLE, STRETCHABLE COILED-SHEET STENT

This application is a continuation of application Ser. No. 09/347,845, filed Sep. 30, 1999, now abandoned the disclosure of which is expressly incorporated herein by reference.

FIELD OF THE INVENTION

The present invention relates generally to prostheses for implantation within body lumens, and more particularly to a coiled-sheet stent including a stretchable mesh design.

BACKGROUND

Tubular prostheses or "stents" are often implanted within blood vessels, for example, within the coronary and carotid arteries, for treating atherosclerotic disease which may involve one or more stenoses. Stents generally have a tubular shape capable of assuming a radially contracted condition to facilitate introduction into a patient's vasculature, and an enlarged condition for engaging the vessel wall at a treatment location. In its contracted condition, the stent may be placed on or in a delivery device, such as a catheter, percutaneously introduced into a patient's vasculature and advanced to a target treatment location. Once at the treatment location, the stent may be deployed and expanded to its enlarged condition, thereby engaging the wall of the vessel and substantially anchoring the stent in place.

Plastically deformable stents have been suggested that are initially provided in their contracted condition, and placed over a balloon on an angioplasty catheter. At the treatment location, the balloon is inflated to plastically deform the stent until it is expanded to its enlarged condition. Thus, the stent may be expanded to any size within a specified range to ensure that the stent substantially engages the wall of the vessel. Plastically deformable stents, however, may not expand uniformly and may not provide a desired delivery profile because of the need for a balloon on the delivery device underlying the stent.

Stents have also been suggested that are self-expanding, i.e., that are biased to assume their enlarged condition but may be radially compressed to a contracted condition. The stent may be mounted to a delivery device and constrained in a contracted condition during delivery, for example, by an overlying sheath. At the treatment location, the stent may be released, for example, by retracting the overlying sheath, the stent automatically resuming its enlarged condition to engage the vessel wall. Such stents, however, may not provide as small a delivery profile as desired and may not anchor against the wall of a vessel as securely as desired, which may lead to migration of the stent within the vessel.

In addition to tubular stents, coiled-sheet stents have been suggested. A flat sheet is provided that is rolled into a spiral shape having overlapping inner and outer longitudinal sections that defines a contracted condition. The coiled-up sheet may be biased to at least partially unroll to assume an enlarged condition, and/or may be caused to unroll and radially expand using a balloon. The coiled-sheet stent may have a nondeformable lattice-like structure and a plurality of fingers or teeth along the inner longitudinal section for engaging openings in the lattice.

Once the coiled-sheet stent is deployed at the treatment location and at least partially expands, a balloon may be introduced within the stent and inflated to further expand the stent to a desired enlarged condition. When the balloon is deflated, the stent may try to radially contract, but the fingers on the inner longitudinal section may then engage corresponding openings in the lattice to lock the stent in the enlarged condition.

Coiled-sheet stents may provide enhanced anchoring within the blood vessel because the size of the fully expanded stent may be more precisely controlled. A coiled-sheet stent, however, may be more rigid transverse to its longitudinal axis than tubular stents, potentially resulting in a less flexible stent, which may not be implanted as effectively in tortuous anatomical conditions. Further, because the lattice-like structure of coiled-sheet stents is substantially nondeformable, if the stent is subjected to radially compressive forces, e.g., when the vessel wall attempts to contract, the stent may tend to buckle rather than recoil from the stress.

Accordingly, there is a need for a stent that provides improved flexibility, while still providing substantial anchoring within a blood vessel.

SUMMARY OF THE INVENTION

The present invention is directed to prostheses for implantation within body lumens, and more particularly to stents including a stretchable mesh design. In accordance with one aspect of the present invention, a stent is provided that includes a generally tubular body having a longitudinal axis and a circumference, and having a size adapted for introduction into a body lumen. A plurality of cylindrical bands are formed in the tubular body, each band having a generally zig-zag pattern including a series of sequential diagonal elements connected to one another and extending about the circumference. A plurality of longitudinal connectors extend between and connect adjacent bands.

The diagonal elements have a generally arcuate shape, all diagonal elements in each band being oriented in either a clockwise or counter-clockwise direction about the circumference for facilitating packing of the diagonal elements in each band with one another. In a preferred form, each diagonal element includes first and second generally straight portions having first and second ends, the second ends being connected together by a curved portion, the first ends being connected to preceding and succeeding diagonal elements in the zig-zag pattern.

In a preferred form, the tubular body is a coiled-sheet, having overlapping inner and outer longitudinal sections. A plurality of teeth or fingers extend from an edge of the inner longitudinal section for engaging openings in the outer longitudinal section. Alternatively, the tubular body may be a plastically deformable or self-expanding tube.

The tubular body is generally expandable between a contracted condition for facilitating introduction into a body lumen, and an enlarged condition for engaging a wall of a body lumen. Preferably, the tubular body is biased towards the enlarged condition. More preferably, the zig-zag pattern is expandable between an unstretched condition and a stretched condition, the zig-zag pattern being biased towards the stretched condition above a transition temperature which is substantially below body temperature, thereby at least partially defining the enlarged condition. Thus, ends of adjacent diagonal elements may be arranged further away from one another about the circumference in the stretched condition than in the unstretched condition. Further, the diagonal elements may have a less arcuate shape in the stretched condition than in the unstretched condition such that the diagonal elements at least partially straighten for minimizing foreshortening of the tubular body along the longitudinal axis.

In accordance with another aspect of the present invention, a stent is provided that has a multi-cellular mesh structure.

The stent includes a generally tubular body having a longitudinal axis and a circumference, a plurality of generally bat shaped cells formed in the tubular body, each cell defining a head region, a tail region and opposing curved wing regions, and a plurality of connectors extending between and connecting adjacent cells.

Preferably, the head region of each cell is connected to the tail region of each circumferentially adjacent cell. For example, the head and tail regions may be directly connected together. Alternatively, a circumferential connector may be provided between the head and tail regions of adjacent cells. The plurality of connectors preferably include a connector extending between a wing region of a first cell and a wing region of an adjacent cell. Alternatively, the wing regions of adjacent cells may be directly connected together.

The cells may be provided in a variety of arrangements both about the circumference and along the longitudinal axis of the tubular body. For example, the head and tail regions may be aligned about the circumference, and the wing regions may have a generally "V" shape extending longitudinally away from the head and tail regions. Preferably, the cells are arranged sequentially about the circumference, thereby defining a cylindrical band. The tubular body may include a plurality of cylindrical bands, each including a sequence of bat shaped cells, adjacent cylindrical bands being connected to one another by longitudinal connectors.

In a preferred form, the wing regions are defined by first and second arcuate members, the first and second arcuate members including a pair of generally straight portions connected to one another by a curved portion. Each head region may then be defined by a longitudinal connector extending between the first arcuate members of the opposing wing regions of the respective cell, and the tail region may be defined by a longitudinal connector extending between the second arcuate members of the opposing wing regions of the respective cell. More preferably, the longitudinal connector of the tail region also defines the longitudinal connector for the head region of an adjacent cell and the longitudinal connector of the head region defines the longitudinal connector for the tail region of an adjacent cell.

The curved wing regions or arcuate diagonal elements are an important feature of a stent in accordance with the present invention as they significantly improve the flexibility of the resulting stent. Conventional coiled-sheet stents, for example, have substantially rigid lattice structures which may not be as flexible transverse to the longitudinal axis of the stent as desired. In contrast, the arcuate diagonal elements of the present invention facilitate flexing of the individual cells generally transverse to the longitudinal axis, the arcuate diagonal elements extending or compressing as needed to facilitate bending of the stent. Thus, the stent may conform more easily to tortuous body regions through which the stent is directed or within which the stent is implanted. In addition, the arcuate diagonal elements may also reduce foreshortening of the stent during expansion.

Other objects and features of the present invention will become apparent from consideration of the following description taken in conjunction with the accompanying drawings.

BRIEF DESCRIPTION OF THE DRAWINGS

FIG. 2 is a detail of a preferred embodiment of a stretchable cell structure.

DETAILED DESCRIPTION OF THE PREFERRED EMBODIMENTS

Figure 1A:
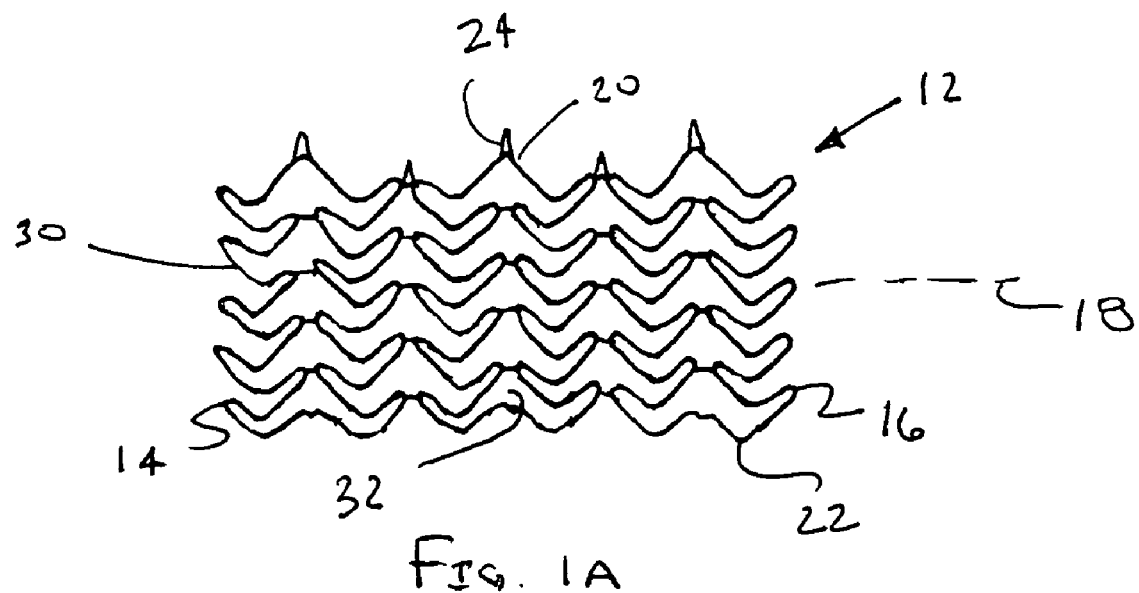
FIG. 1A is a side view of an unrolled coiled-sheet for a stretchable coiled-sheet stent, in accordance with one aspect of the present invention.
Figure 1B:
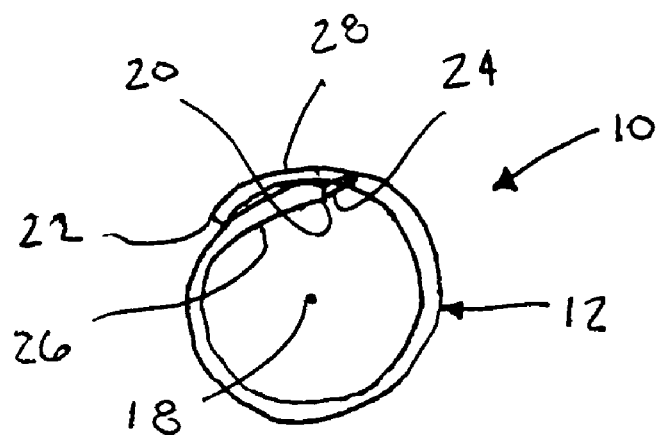
FIG. 1B is an end view of the coiled-sheet of FIG. 1A rolled into a coiled-sheet stent.

Turning now to the drawings, FIGS. 1A and 1B show a preferred embodiment of a coiled-sheet stent 10, in accordance with one aspect of the present invention. The coiled-sheet stent 10 is formed from a substantially flat sheet 12 having first and second ends 14, 16 defining a longitudinal axis 18 therebetween. The sheet 12 also includes first and second longitudinal edges 20, 22, the first edge 20 having a plurality of fingers or teeth 24 extending therefrom substantially perpendicular to the longitudinal axis 18.

The sheet 12 also includes a plurality of stretchable elements 30 formed therein, thereby defining a multi-cellular mesh structure capable of expanding and/or contracting in a direction substantially perpendicular to the longitudinal axis 18. Preferably, the stretchable elements 30 define a lattice-like structure providing a plurality of openings 32 for receiving the teeth 24, as described further below. The stretchable elements 30 may be elastically deformable, i.e., biased to assume a first shape but temporarily deformable from that first shape, and/or may be plastically deformable, i.e., assuming any shape to which the stretchable elements 30 are deformed.

As best seen in FIG. 1B, the sheet 12 is preferably provided in a coiled-up condition, defining overlapping inner and outer longitudinal sections 26, 28 that may slide with respect to one another to allow radial expansion of the coiled-sheet 12 between a contracted condition and one or more enlarged conditions. The coiled-up sheet 12 may be biased to the contracted condition, thereby requiring a balloon or other expandable member to radially expand the stent 10 to the enlarged condition, and/or the coiled-sheet 12 may be biased to at least partially unroll to allow radial expansion.

In a preferred form, the stretchable elements 30 have a temperature-activated shape memory. For example, at a first temperature, the stretchable elements 30 may be biased to assume a circumferentially contracted or "unstretched" shape, while at a higher second temperature, e.g., above a transition temperature for the stent material, the stretchable elements 30 may become biased to assume a circumferentially expanded or "stretched" shape. Preferably, the first temperature is generally about ambient temperature, such as about 25 degrees Celsius or less, and the second temperature is generally about body temperature, such as about 37 degrees Celsius or higher.

To manufacture a coiled-sheet stent 10 as described, a relatively thin, substantially flat sheet 12 is provided formed from a biocompatible material, such as stainless steel or a polymer. More preferably, the sheet 12 is formed from a shape memory polymer or metal, such as a nickel-titanium alloy ("Nitinol"), more preferably having a thermally-activated shape memory. Alternatively, an elastic material, such as tantalum, platinum or tungsten alloy, or a super-elastic material, such as Nitinol, may be used. The stretchable elements 30, the teeth 24 and/or any other openings in the sheet 12 may be formed using a number of conventional metal working processes, such as die and punch, laser cutting, or chemical etching.

In one preferred method, the stretchable elements 30 are formed in their stretched shape and the sheet 12 is subsequently heat treated, for example, to a temperature of about 500 degrees Celsius or higher, to activate the shape memory of the material. After the sheet 12 has cooled, the stretchable elements 30 are compressed into their unstretched shape, and the sheet 12 is rolled to provide a coiled-sheet stent 10.

Preferably, the sheet is formed from Nitinol which, when heat treated, is converted substantially to its austenitic phase, i.e., set to assume its stretched shape. As it is cooled, the Nitinol material preferably undergoes martensitic transformation. When the stretchable elements 30 are compressed, for example, at ambient temperatures, into their unstretched shape, the material is substantially martensite which is plastically deformed into the unstretched condition. More preferably, a Nitinol alloy is selected such that transformation back to austenite occurs by the time the material reaches body temperature, e.g., about 37 degrees Celsius. Thus, the stretchable elements 30 may automatically become biased to resume the stretched shape upon reaching body temperature.

In another preferred method, the stretchable elements 30 may be formed in their unstretched shape, and then plastically deformed to their stretched shape, e.g., while the Nitinol material is in its martensitic phase. The sheet 12 may then be heat treated, e.g., to transform the material to its austenitic phase, thereby storing the stretched shape in the material's shape memory. Upon cooling, the material will transform back to martensite, thereby returning to the unstretched shape. The sheet 12 may then be rolled into its contracted condition for placement on a delivery device (not shown).

The coiled-sheet stent 10, in its contracted condition, may be placed over the distal end of a delivery catheter (not shown) having a size adapted for percutaneous introduction into a patient's vasculature. A retractable sheath (not shown) may be advanced over the distal end, thereby protecting the stent 10, preventing shifting and/or preventing premature deployment. Alternatively, other mechanisms may be provided for constraining the stent 10 in its contracted condition, such as a wire or thread (not shown) which may be woven through overlapping layers of the stent to prevent premature unrolling.

The distal end of the catheter-sheath assembly may then be percutaneously introduced into a patient's vasculature, and advanced to a target treatment location, such as a stenosis within the carotid or coronary arteries. As the stent 10 reaches body temperature within the patient, the transition temperature of the stent material is surpassed, thereby activating the temperature-activated shape memory of the material such that the stretchable elements 30 become biased to assume their stretched shape, e.g., when the Nitinol completes transformation back to austenite. Thus, the sheath constrains the stent 10 from at least partially expanding because of the stretching of the stretchable elements 30. Once the stent 10 is properly positioned at the treatment location, the sheath may be retracted, thereby exposing the stent 10, which may then at least partially expand radially as the stretchable elements 30 assume their stretched shape.

The catheter-sheath assembly may be withdrawn, and a balloon catheter (not shown) may be introduced into the interior of the partially expanded stent 10. Alternatively, a balloon or other expandable member (not shown) may be provided on the delivery catheter adjacent to the stent 10. The balloon may be inflated, thereby further radially expanding the stent 10. Once a desired enlarged condition is achieved, the balloon is deflated and withdrawn. Preferably, the teeth 24 on the inner longitudinal edge 20 engage a set of the openings 32 in the sheet 12, thereby substantially locking the stent 10 in its enlarged condition. Thus, the teeth 24 allow the stent 10 to be ratcheted to a number of enlarged conditions as long as the inner and outer longitudinal sections 26, 28 overlap and allow the teeth 24 to engage corresponding openings 32, as will be appreciated by those skilled in the art.

In addition, the coiled-sheet stent may also include outwardly-oriented hooks or barbs (not shown) for enhancing anchoring of the stent within a body passage. Pro-thrombotic material (not shown) may be provided on the exterior surfaces of the coiled-sheet stent to enhance sealing against the wall of the body passage. Additional information on coiled-sheet stents appropriate for use with the present invention may be found, for example, in U.S. Pat. Nos. 4,577,631 issued Mar. 25, 1986 in the name of Kreamer, U.S. Pat. No. 5,007,926 issued Apr. 16, 1991 in the name of Derbyshire, U.S. Pat. No. 5,158,548 issued Oct. 28, 1992 in the name of Lau et al., U.S. Pat. Re 34,327 reissued Jul. 27, 1993 in the name of Kreamer, U.S. Pat. No. 5,423,885 issued Jun. 13, 1995 in the name of Williams, U.S. Pat. No. 5,441,515 issued Aug. 15, 1995 in the name of Khosravi et al., and U.S. Pat. No. 5,443,500 issued Aug. 22, 1995 in the name of Sigwart. The disclosures of these references and any others cited therein are expressly incorporated herein by reference.

The stretchable elements included in a coiled-sheet stent in accordance with the present invention may take on a number of different forms. Generally, a plurality of stretchable elements are provided in a predetermined arrangement, such as a longitudinal or circumferential configuration, although a variety of arrangements providing a desired recoil or flexibility characteristic may be provided application Ser. No. 09/192,977, filed Nov. 16, 1998, the disclosure of which is expressly incorporated herein by reference, discloses a number of such arrangements.

Thus, each stretchable element generally defines an individual, "cell," thereby providing a multi-cellular structure when the individual cells are duplicated in a predetermined pattern, as in the preferred embodiment described below. As used herein, the terms "longitudinal" and "longitudinally" refer to those elements in each individual cell oriented towards the ends of the stent, i.e., arranged generally along the longitudinal axis. The terms "circumferential" and "circumferentially" refer to those elements oriented about the periphery or circumference of the stent, i.e., arranged generally perpendicular to the longitudinal axis.

Turning to FIG. 2, a preferred embodiment of a multi-cellular mesh structure 40 is shown which includes a plurality of cells 42 having a shape which may be described as similar to a bat. Each cell 42 defines a "head" region 44, a "tail" region 46, and first and second curved "wing" regions 48, 50 which make up the bat shape. The head region 44 of each cell is connected to the tail region 46' of the adjacent cell 42'. Preferably, the adjacent cells 42, 42' are directly connected, as shown, although alternatively, one or more circumferential connectors (not shown) may be provided that extend circumferentially between the adjacent head and tail regions.

The head and tail regions 44, 46 are preferably aligned circumferentially, i.e., defining a circumferential axis 52 substantially perpendicular to the longitudinal axis 18, and the wing regions 48, 50 preferably have a generally "V" shape extending longitudinally away from the head and tail regions 46, 48, i.e., opposing one another about the circumferential axis 52.

The wing regions 48, 50 are preferably defined by first and second arcuate members 54, 56, the arcuate members 54, 56 each including first and second generally straight portions 54a, 54c, 56a, 56c connected to one another by a curved portion 54b, 56b. Preferably, the second straight portion 54c is substantially shorter than the first straight portion 54c of the first arcuate member 54, and similarly, the first straight portion 56a is substantially shorter than the second straight portion 56c of the second arcuate member 56, as may be seen in FIG. 2. Each head region 44 is preferably defined by a longitudinal connector 58 extending between the first generally straight portions 54*a* of the first arcuate members 54 of the opposing wing regions 48, 50. Similarly, the tail region is preferably defined by a longitudinal connector 60 extending between the first generally straight portions 56*a* of the second arcuate members 56.

Preferably, the ends of the second generally straight portions 54*c*, 56*c* are connected to one another opposite the curved portions 54*b*, 56*b* by curved loop portions 62, thereby defining tips of the wing regions 48, 50. In addition, the ends of the first generally straight portions 54*a*, 56*a* may be connected opposite the curved portions 54*b*, 56*b* to first generally straight portions 56*a'*, 54*a''* of the circumferentially adjacent cells 42', 42'', respectively, by loop portions 64. This structure results in the longitudinal connector 58 of the head region 44 also being the longitudinal connector for the tail region 46' of the adjacent cell 42' and the longitudinal connector 60 of the tail region 46 being the longitudinal connector for the circumferentially adjacent head region 44''.

As shown in FIGS. 1A and 1B, when a sheet 12 having bat shaped cells formed therein (not shown) is rolled into a coiled-sheet stent 10, each circumferential sequence of wing regions 48, 48', etc. or 50, 50', etc. defines a cylindrical band 70. Each cylindrical band 70 has a generally zig-zag pattern defined by a series of sequential diagonal elements, namely the alternating first and second arcuate members 54, 56, connected to one another by loop portions 62, 64.

Within each cylindrical band, 70, all of the diagonal elements 54, 56 are preferably oriented in either a "clockwise" or "counter-clockwise" direction about the circumference. Stated differently, the curved portions 54*b*, 56*b* are all aligned in each band 70 such that they generally "point" in a single direction about the longitudinal axis 18, as viewed from FIG. 1B, for example, or parallel to the circumferential axis 52, as viewed from FIG. 2. Thus, the curved portions 54*b*, 56*b* define apices in the generally "V" shaped wing regions 48, 50 which point about the longitudinal axis 18 in either a clockwise or counter-clockwise direction. This feature may be important to facilitate "packing" of the diagonal elements 54, 56 in each cell with one another, i.e., for compressing the diagonal elements 54, 56 when the coiled-sheet stent is in its unstretched condition without causing overlapping of the diagonal elements 54, 56.

More preferably, all of the diagonal elements 54, 56 in all of the cells of the stent are preferably oriented clockwise, as viewed from FIG. 1B. Thus, the curved portions 54*b*, 56*b* of underlying diagonal elements 54, 56 may be oriented away from overlying diagonal elements 54, 56, which may substantially reduce the risk of underlying diagonal elements catching on overlying diagonal elements during expansion.

The arcuate diagonal elements (or curved wing regions) are an important feature of the present invention, because of the flexibility they provide to the overall mesh structure of the coiled-sheet stent. Coiled-sheet stents having rigid grid mesh structures may not provide sufficient flexibility generally transverse to the longitudinal axis of the stent. In contrast, the arcuate diagonal elements allow the individual cells to flex generally transverse to the longitudinal axis, the arcuate diagonal elements extending or compressing as needed. Thus, the stent may conform more easily to tortuous body regions through which the stent is directed or within which the stent is implanted.

In addition, the arcuate diagonal elements may also reduce foreshortening of the stent during expansion. Diamond shaped mesh structures, for example, may substantially foreshorten longitudinally as they expand radially. The cell structure of the present invention, in contrast, may substantially reduce such foreshortening. During expansion, adjacent diagonal elements move away from one another in the circumferential direction, i.e., parallel to the circumferential axis 52, thereby tending to reduce the longitudinal component of the diagonal elements. To compensate for at least some of this reduction, the curved portion 54*b*, 56*b* of the diagonal elements 54, 56 may yield, increasing an inside angle 66, 68 between the first and second straight portions 54*a*, 56*a*, 54*c*, 56*c* of the respective diagonal elements 54, 56 and thereby increasing the longitudinal component of the diagonal elements 54, 56.

In a preferred form, the longitudinal connectors 58, 60 have a length that is substantially less than the longitudinal component of the arcuate diagonal elements 54, 56, thereby ensuring effective scaffolding of the body lumen during expansion. Alternatively, the longitudinal connectors 58, 60 may have a length as long as or greater than the longitudinal component of the diagonal elements 54, 56, although this may be disfavored because of the gaps that may occur within the multicellular structure.

In a further alternative, the longitudinal connectors may include curved portions that may provide additional flexibility between the adjacent cylindrical cells. The flexible nature of the arcuate diagonal elements and curved wing regions, however, preferably provide sufficient flexibility such that substantially straight longitudinal connectors may be provided that extend substantially parallel to the longitudinal axis. The longitudinal connectors may bend, either where they connect to the diagonal elements or at an intermediate point, when the stent is bent transverse to the longitudinal axis to provide additional flexibility.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A stent, comprising:
a generally tubular body having a longitudinal axis and a circumference, and having a size adapted for introduction into a body lumen, wherein said tubular body comprises a coiled-sheet,
said tubular body consisting essentially of a series of generally non-sinusoidal cylindrical bands and a plurality of straight, generally non-sinusoidal, longitudinal connectors extending between and connecting adjacent cylindrical bands, each longitudinal connector having a length, each cylindrical band comprising a series of diagonal elements connected to one another and extending about the circumference, wherein each diagonal element comprises first and second generally straight portions having first and second ends, the second ends being connected together in a curved portion, the first ends being connected to preceding and succeeding diagonal elements, and wherein each longitudinal connector consists of a straight segment that extends between longitudinally separated curved portions, and
wherein all of the diagonal elements in all of the cylindrical bands comprising the tubular body are oriented in a clockwise direction about the circumference.

2. The stent of claim 1, wherein the tubular body is expandable between a contracted condition for facilitating introduction into a body lumen and an enlarged condition for engaging a wall of a body lumen.

3. The stent of claim 2, wherein the tubular body is biased toward the enlarged condition.

4. The stent of claim 2, wherein the cylindrical bands are expandable between an unstretched condition and a stretched condition, the cylindrical bands being biased toward the stretched condition above a transition temperature that is substantially below body temperature, thereby at least partially defining the enlarged condition.

5. The stent of claim 4, wherein ends of adjacent diagonal elements are arranged further away from one another about the circumference in the stretched condition than in the unstretched condition.

6. The stent of claim 1, wherein the longitudinal connectors have a longitudinal dimension that is substantially smaller than a longitudinal dimension of the diagonal elements.

7. The stent of claim 1, wherein the diagonal elements of each cylindrical band are out of phase with any adjacent cylindrical band.

8. The stent of claim 1, wherein each longitudinal connector extends substantially parallel to the longitudinal axis.

9. A stent, comprising:
a generally tubular body having a longitudinal axis and a circumference, and having a size adapted for introduction into a body lumen, wherein the tubular body comprises a coiled-sheet,
said tubular body consisting of a plurality of cylindrical bands, each cylindrical band consisting of a sequence of bat-shaped cells, each of said generally bat-shaped cells formed from a plurality of generally non-sinusoidal cylindrical bands and a plurality of straight, generally non-sinusoidal, longitudinal connectors extending between and connecting adjacent cylindrical bands in the tubular body, each longitudinal connector having a length, each cell defining a head region, a tail region and opposing curved wing regions, the head region of each cell being connected to the connected to the tail region of an adjacent cell, wherein each head region is defined by a longitudinal connector, and wherein each tail region is defined by a longitudinal connector,
wherein the wing regions are defined by first and second arcuate members, the first and second arcuate members comprising a pair of generally straight portions connected to one another by a curved portion,
wherein the curved portion defines an apex of the curved wing regions, the apices all pointing substantially in a single direction; and
wherein each longitudinal connector consists of a straight segment.

10. The stent of claim 9 wherein the head and tail regions are aligned about the circumference, and the wing regions have a generally "V" shape extending longitudinally away from the head and tail regions.

11. The stent of claim 10, wherein the cells are arranged sequentially about the circumference, thereby defining a cylindrical band.

12. The stent of claim 9, wherein the longitudinal connector defining each head region extends between the first arcuate members of the opposing wing regions of the respective cell, and longitudinal connector defining each tail region extends between the second arcuate members of the opposing wing regions of the respective cell.

13. The stent of claim 12, wherein one of the generally straight portions of each of the first and second arcuate members is substantially shorter than the other generally straight portion of the respective arcuate member.

14. The stent of claim 12, wherein the longitudinal connector defining the tail region also defines the head region of an adjacent cell.

15. The stent of claim 9, wherein the plurality of connectors comprise a longitudinal connector extending between a wing region of a first cell and a wing region of an adjacent cell.

16. The stent of claim 9, wherein the tubular body is expandable between a contracted condition for facilitating introduction into a body lumen and an enlarged condition for engaging a wall of a body lumen.

17. The stent of claim 16, wherein the tubular body is biased towards the enlarged condition.

* * * * *